United States Patent [19]

Hanover et al.

[11] Patent Number: 5,196,002
[45] Date of Patent: Mar. 23, 1993

[54] IMPLANTABLE DRUG DELIVERY SYSTEM WITH PISTON ACUTATION

[75] Inventors: Barry K. Hanover; Stephen C. Jacobsen; Eric M. Simon; Tomasz Petelenz, all of Salt Lake City; Michael G. Mladejovsky, Murray, all of Utah

[73] Assignee: University of Utah Research Foundation, Salt Lake City, Utah

[21] Appl. No.: 716,926

[22] Filed: Jun. 18, 1991

Related U.S. Application Data

[62] Division of Ser. No. 594,271, Oct. 9, 1990, Pat. No. 5,059,175.

[51] Int. Cl.$^5$ .............................................. A61K 9/22
[52] U.S. Cl. ................................. 604/891.1; 604/135; 604/246
[58] Field of Search ................ 128/202.26; 604/890.1, 604/891.1, 27, 28, 30, 31, 141, 142, 143, 145, 246, 131, 134, 135, 207, 208, 114

[56] References Cited

U.S. PATENT DOCUMENTS

| 640,868 | 1/1900 | Bring | 604/135 |
|---|---|---|---|
| 2,183,482 | 12/1939 | Kurkgian | 604/135 |
| 3,840,009 | 10/1974 | Michaels et al. | |
| 3,923,060 | 12/1978 | Ellinwood, Jr. | 604/891.1 |
| 4,239,040 | 12/1980 | Hosoya et al. | 604/135 |
| 4,312,347 | 1/1982 | Magoon et al. | |
| 4,313,439 | 2/1982 | Babb et al. | 604/135 |
| 4,326,522 | 4/1982 | Guerrero et al. | |
| 4,425,117 | 1/1984 | Hugemann et al. | |
| 4,439,197 | 3/1984 | Honda et al. | |
| 4,457,752 | 7/1984 | Vadasz | 604/135 |
| 4,564,363 | 1/1986 | Bagnall et al. | 604/891.1 |
| 4,714,962 | 12/1987 | Di Domenico | 604/891.1 |

Primary Examiner—Randall L. Green
Assistant Examiner—K. M. Reichle
Attorney, Agent, or Firm—Thorpe North & Western

[57] ABSTRACT

An implantable drug delivery system includes a housing having a base end and a discharge end, for holding drug solution at the discharge end, a valve disposed at the discharge end to allow a drug solution to flow from inside the housing, through the valve and out of the housing when solution pressure is applied to the valve, a piston slidably disposed in the housing to slide between the base end and discharge end to force solution toward the discharge end and out the valve, and a spring disposed in the housing between the piston and the base end thereof for urging the piston toward the discharge end. A plurality of different length tethers are connected at one end to the piston and at the other end to a respective release node located at the base end of the housing. Each release node holds the other end of a respective one of the tethers until a release signal is received at which time it releases the tether. A timing circuit is disposed in the housing at the base end to supply release signals sequentially to the nodes in order of the shortest tether node to the longest tether node so that as a tether is released, the piston is allowed to move toward the discharge end of the housing to thereby discharge or bolus of drug solution from the housing, until the next shortest unreleased tether stops further movement of the piston.

7 Claims, 2 Drawing Sheets

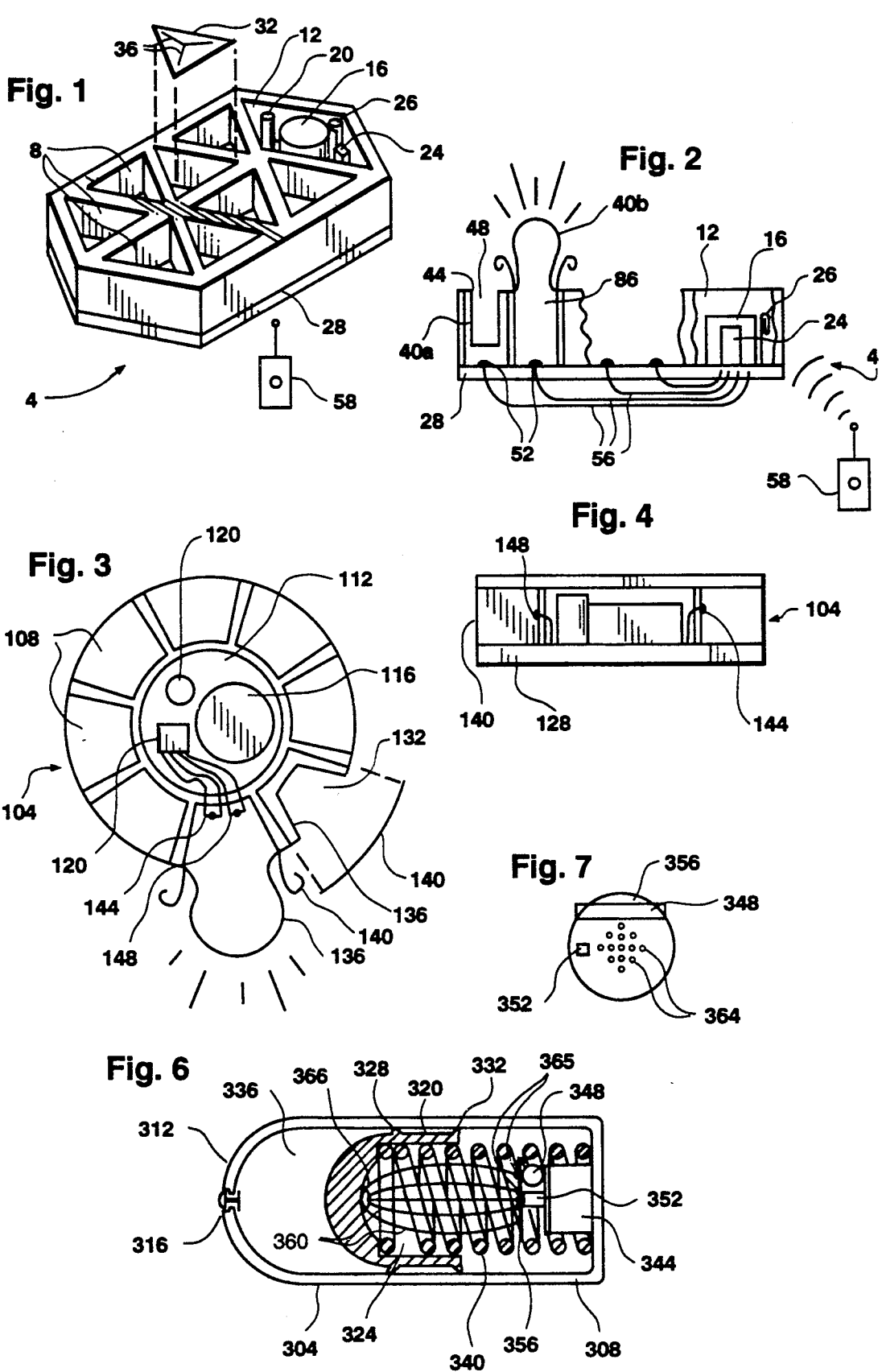

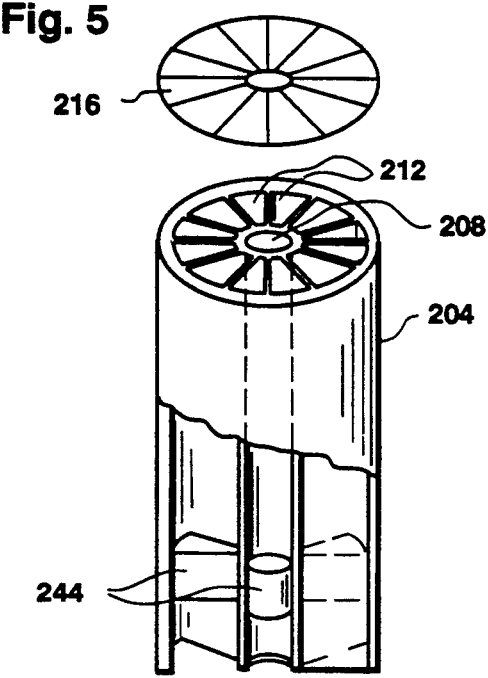
Fig. 5
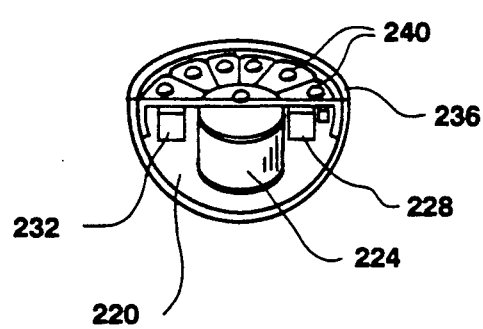
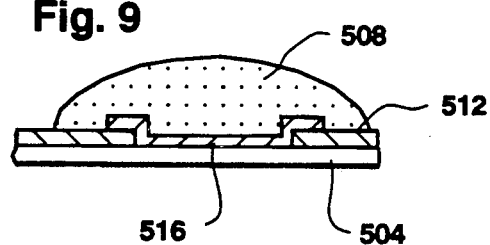
Fig. 9
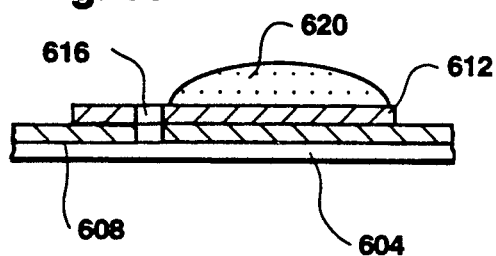
Fig. 11
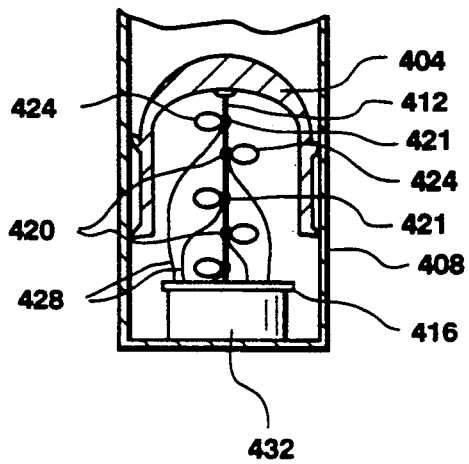
Fig. 8
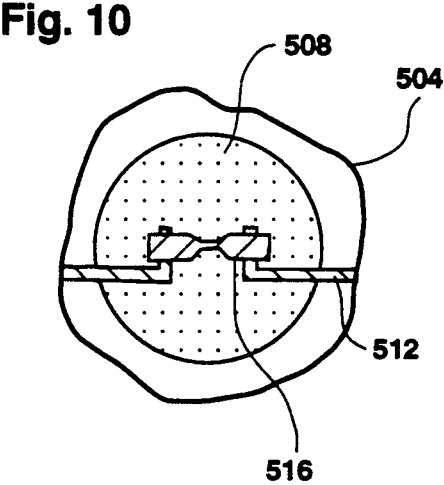
Fig. 10
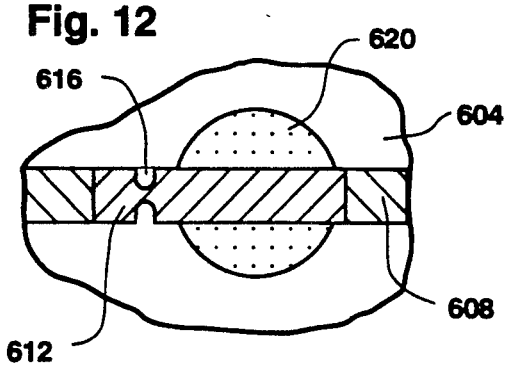
Fig. 12

5,196,002

IMPLANTABLE DRUG DELIVERY SYSTEM WITH PISTON ACUTATION

This is a division of application Ser. No. 07/594,271 filed Oct. 9, 1990, now U.S. Pat. No. 5,059,175.

BACKGROUND OF THE INVENTION

The present invention relates to simple and efficient piston-actuated drug delivery systems for implantation into an animal or human for delivery of drug to the animal or human incrementally over some period of time.

It is well known in the fields of animal husbandry and veterinary medicine that it is desirable and in some instances necessary to treat or care for farm animals by periodically injecting the animals (or administering orally) with various drugs If a series of injections or other administrations are required, this may require finding and rounding up the animals, administering the desired drug (or different drugs), and then releasing the animals until the next drug administration is due. Of course, it can be time consuming and costly, each time treatment of a farm animal is required, to locate the farm animal and bring it to a suitable location for treatment. It has been proposed that drug delivery devices be implanted in farm animals for the periodic release of drugs, examples of such devices being disclosed in U.S. Pat. Nos. 4,564,363, 4,326,522, 4,425,117, 4,439,197, 3,840,009, 4,312,347 and 4,457,752.

Although the devices disclosed in the above-cited patents serve to deliver a drug or solution to the body of an animal or person in which they are located, the devices are typically limited to specific applications, allow for a onetime discharge (a continuous delivery) of drug into the system of the body in which the device is located, are bulky and therefore difficult to place and maintain in the body, or are complicated and costly to manufacture and use.

SUMMARY OF THE INVENTION

It is an object of the invention to provide a simple and efficient drug delivery system which may be implanted in the body of an animal or human for timed, periodic release of the drug into the body.

It is also an object of the invention to provide such a drug delivery system which is compact and can be readily manufactured.

It is a further object of the invention to provide such a drug delivery system which has a high ratio of drug volume to housing or package volume.

It is an additional object of the invention to provide such a drug delivery system which is reliable and substantially leak free.

The above and other objects of the invention are realized in a specific illustrative embodiment of an implantable drug delivery system which includes a housing having a base end and a discharge end, for holding drug formulation at the discharge end, a one-way valve disposed at the discharge end to allow formulation to flow or move through the valve and out of the housing when formulation pressure is applied to the valve, a piston slidably disposed in the housing to slide between the base end and discharge end to force formulation toward the discharge end and out the valve, and a biasing element for urging the piston toward the discharge end of the housing. Also included is a restraining member for allowing successive step-wise movement of the piston toward the discharge end of the housing in response to release signals, but for otherwise restraining movement of the piston. A control unit located at the base end of the housing supplies release signals to the restraining member in a predetermined sequence so that drug formulation is successively forced out of the housing in discreet amounts.

BRIEF DESCRIPTION OF THE DRAWINGS

The above and other objects, features and advantages of the invention will become apparent from a consideration of the following detailed description presented in connection with the accompanying drawings in which:

FIG. 1 is a perspective view of an implantable drug delivery multiple-vesicle device made in accordance with the principles of the present invention;

FIG. 2 is a side, fragmented, cross-sectional view of the device of FIG. 1;

FIG. 3 is a top, plan, cross-sectional view of another embodiment of a multiple-vesicle drug delivery system made in accordance with the principles of the present invention;

FIG. 4 is a side view of the embodiment of FIG. 3 but showing only a few of the component parts;

FIG. 5 is an isometric, exploded, partially cutaway view of still another embodiment of a drug delivery system made in accordance with the principles of the present invention and utilizing piston or plunger discharge elements in multiple vesicles;

FIG. 6 is a side, cross-sectional view of still another embodiment of a drug delivery system made in accordance with the principles of the present invention and utilizing a plunger in a single cylindrical vesicle;

FIG. 7 is a top, plan view of the release mechanism of FIG. 6;

FIG. 8 is a fragmented, side, cross-sectional view of another embodiment of a drug delivery system made in accordance with the principles of the present invention;

FIG. 9 is a side, elevational view of one embodiment of a pyrotechnic gas generating element made in accordance with the present invention;

FIG. 10 is a top plan view of the embodiment of FIG. 9;

FIG. 11 is a side, elevational view of another embodiment of a pyrotechnic gas generating element made in accordance with the present invention; and FIG. 12 is a top plan view of the embodiment of FIG. 11.

DETAILED DESCRIPTION

Referring to FIGS. 1 and 2 of the drawings, there is shown a low profile, compact drug delivery system made in accordance with the present invention to include a housing 4 having formed therein two (or more) rows of vesicles or compartments 8, each having top, polygonally shaped cross-sections to allow compact nesting together of the compartments. The compartments shown in the FIGS. 1 and 2 embodiment have triangular top cross sections, but other shapes could also be used to achieve the desired nesting.

Positioned at one end of the two rows of compartments 8 is a utility compartment 12 in which is housed a battery 16, an oscillator 20, a timing circuit 24, and a receiver and antenna 26. The elements 16, 20, 24 and 26 are mounted on a substrate 28 which forms the floor of the utility compartment 12 and the other compartments 8.

Each compartment 8 has an opening at the top which is covered by a rupturable cover, such as the one cover 32 shown. The covers 32 might illustratively be made of a thin metal foil or might be made of a thin plastic sheet. Score lines 36 may be formed in the cover 32 to more readily facilitate the rupture of the cover and the release of the contents of the corresponding compartment (to be discussed momentarily). The housing 4 might advantageously be made of injection molded polycarbonate or other plastics. The substrate 28 might illustratively be made of conventional circuit board material such as a fiberglass and epoxy composite or polyamide film, for carrying the circuit component 16, 20, 24 and 26 and electrical conductors to be discussed later.

Disposed in each compartment 8 is a corresponding drug containment sack (FIG. 2 at 40a and 40b) having a mouth 44 which circumscribes an opening 48 to the interior of the sack (see FIG. 2). The mouth 44 of each drug containment sack is attached to the opening of the corresponding compartment, at the top thereof, to seal the inside of each sack from the inside of the corresponding compartment. The drug containment sacks are provided for holding drug solution (or powder or granular formulation) to be delivered to an animal into which the drug delivery system is implanted. The sacks 40a and 40b might illustratively be made of polyvinylidene chloride, fluorinated ethylene-propylene, or other suitably flexible and fluid and chemical impervious material.

Disposed at the bottom of each compartment on the substrate 28 is a pyrotechnic gas generating element, typically a bead of material 52 which is responsive to heat resulting from an electrical signal applied to a heating element, thereby igniting and producing gas for filling the corresponding compartment. Alternatively, a non-toxic foam may be produced by an ignition material to similarly fill a corresponding compartment. As a compartment fills with gas, the gas forces the corresponding drug containment sack upwardly and the sack, in turn, forces drug solution against a corresponding cover 32 to rupture the cover and allow the drug solution and sack to be emitted from the compartment. Sack 40b of FIG. 2 is shown fully pushed out of the compartment 8b which ensures that all drug solution initially contained in the sack is released into the animal.

The pyrotechnic gas generating material 52 might illustratively be a composition of nitrocellulose or polyvinyl nitrate. Although not shown, a second pyrotechnic gas generating bead might also be included in each compartment to be activated after the first bead has been activated to thereby better ensure the complete release of drug solution from each compartment.

The timing circuit 24 operates in response to a remotely transmitted signal (transmitted by a transmitter 58) received by the receiver and antenna 26 to selectively and sequentially connect the battery 16 by way of electrical conductors 56 to the pyrotechnic gas generating beads 52. Remotely transmitted signals could be used simply to initiate operation of the timing circuit 24 which would then periodically activate selected gas generating beads 52 on its own, or the transmitted signals could be used to directly activate a bead with each transmitted signal. (Although the conductors 56 are shown as being under the substrate 28 in FIG. 2, this is for illustrative purposes only and it should be understood that the conductors would be formed upon the substrate by conventional photo-lithographic, vacuum deposition, or other conventional conductor forming techniques.) The conductors 56 could illustratively be made of a relatively low resistance conductive ink made, for example, of a resin and carbon and silver particles. An alternative to initiating operation of the timing circuit 24 by radio or other signal transmission would be simply to internally set the timing circuit to begin operation some predetermined time in the future—e.g., after supplying the drug delivery system to an animal.

The oscillator 20 supplies an oscillatory signal to the timing circuit 24 which is adapted to selectively connect the battery 16 to the pyrotechnic gas generating beads 52 in some preferred order (to activate the beads) and with a predetermined delay between activation of the different beads, to thereby discharge boluses of drug solution into the animal over a period of time.

FIGS. 3 and 4 show another embodiment of a drug delivery system having a short, cylindrically-shaped housing 104 having a plurality of compartments 108 formed in a circle about a central utility compartment 112. The utility compartment 112 again includes a battery 116, an oscillator 120 and a timing circuit 124, all mounted on a substrate 128 which forms a common floor for the utility compartment 112 and the other compartments 108. (A receiver and antenna could also be provided for this embodiment as well as the other embodiments, for remote operation, as explained for the FIGS. 1 and 2 embodiment.)

Although the compartments 108 could have openings at the top of the housing 104, similar to the embodiment of FIGS. 1 and 2, the compartments are shown as having openings 132 in the circumferential outer wall of the housing. Drug containment sacks 136 are disposed in each compartment for holding a drug solution, and rupturable covers 140 are disposed over the compartment openings as best seen in FIG. 3. Alternatively to placing individual covers 140 over each of the compartment openings, a single strip cover could be disposed at the circumferential outer side of the housing 104 to cover all of the openings, with appropriate scoring of the cover being made to allow release of drug solution only from those compartments which are activated. A pair of individually activatable pyrotechnic gas generating beads 144 and 148 (FIG. 3) are disposed in each compartment on the wall opposite the compartment opening (or on the substrate floor), for producing gas to discharge the contents of the compartment in response to an electrical ignition signal.

FIG. 5 shows an isometric, exploded, partially cutaway view of a drug delivery system having an elongate, tubular housing 204. Formed in the housing is a central compartment or vesicle 208, and a plurality of other vesicles 212 disposed in a circle about the central vesicle as shown. The vesicles extend along a substantial length of the housing 204 generally in parallel with one another and include openings at the upper end of the housing. A rupturable cover 216 is disposed over the upper end of the housing to cover the openings of the vesicles, but to also rupture and allow discharge of the contents of a vesicle when a certain fluid pressure is supplied to the cover from inside the vesicle. Although the vesicles 212 are shown to be generally the same size, different size vesicles could be provided to allow for delivery of different amounts of drug—both of this embodiment and the others.

The housing 204 also includes a bottom compartment 220 in which are disposed a battery 224, an oscillator 228 and a timing circuit 232. The compartment 220 is separated from the vesicles 208 and 212 by a floor or substrate 236 in which are located a plurality of pyrotechnic gas generating beads 240. The circuit components 224, 228 and 232 selectively and successively ignite the pyrotechnic gas generating beads 240 in the same manner as discussed for the embodiments of FIGS. 1 and 2 and FIGS. 3 and 4.

Disposed in each vesicle 208 and 212 near the bottoms thereof are pistons or plungers 244. The side surfaces of the plungers 244 are shaped to conform to and snugly fit within the side walls of the corresponding vesicles so that as a plunger is forced upwardly in a vesicle by gas pressure, it pushes out of the housing a drug formulation contained in the vesicle. The plungers 244 are forced upwardly in the corresponding vesicles by the activation of the pyrotechnic gas generating beads (or other geometric shapes) 240.

Advantageously, the plungers 244 are made of polyurethane, synthetic rubber or paraffin which will allow for a slidably tight fit within the vesicles and will also provide some lubrication to facilitate the sliding of the plungers. The housing 204 could illustratively be made of injection molded polycarbonate.

FIGS. 6 and 7 show respectively a side, cross-sectional view of another embodiment of an implantable drug delivery system, and a top plan view of the release mechanism of the system. The FIGS. 6 and 7 system include a housing 304 having a base end 308 and a discharge end 312. A passive one-way valve 316 is disposed in the discharge end of the housing to allow release of drug formulation contained in the housing when a certain fluid pressure is applied from inside the housing to the valve.

Disposed in the housing is a piston or plunger 320 having a spring receiving hollow 324 on the underneath side thereof. The exterior side wall of the plunger 320 includes axially spaced apart wipers or seals 328 and 332 for making intimate but slidable contact with the interior side wall of the housing 304. The plunger 320 is positioned in the housing 304 initially at a location to define a cavity or reservoir 336 above the plunger for holding a drug formulation.

Also disposed in the housing 304 is a coil spring 340 which extends from a bottom wall at the base end of the housing 308 upwardly into the hollow 324 of the plunger 320. A battery 344, oscillator 348 and timing circuit 352 are disposed within the coil spring 340 on the bottom wall of the housing (but could also be disposed in the plunger 320). Disposed above the circuit elements 344, 348 and 352 is a release circuit card 356 (a bottom view being shown in FIG. 7 with the oscillator 348 and timing circuit 352 mounted thereon). The battery 344, oscillator 348, and timing circuit 352 function as do the earlier described corresponding components to provide a release signal(s) and serve as the presently preferred example of a means for supplying a predetermined sequence of release signals. It will be appreciated that arrangements other than the described circuit components can serve as the release signal supplying means of the present invention.

A plurality of different length tethers or fibers 360 are attached at one end to the underside of the plunger 320 and at the other end to release nodes 364 disposed on the circuit card 356. The tethers 360 serve to hold the plunger in place and prevent it from being moved upwardly toward the discharge end of the housing by the spring 340 until selected tethers are released from the circuit cards. In particular, each of the tethers, being a different length, serve to hold or retain the plunger 320 at different distances away from the circuit card 356 until the tether holding the plunger at a respective length is released from its corresponding release node 364. In this manner, the tethers 360 can be successively released to allow a stepwise movement upwardly of the plunger 320 to successively discharge boluses of drug formulation contained in the reservoir 336.

The release nodes 364 are composed of a material (e.g., ultra-high-modulus polyethylene) capable of holding the ends of the respective tethers 360 until the material is activated or ignited (for example by a pyrotechnic material represented at 365) in response to an electrical signal to either sever or release the corresponding tether end. The pyrotechnic material 365 responds to electrical signals, referred to as "release signals," generated by the described electrical components. Each release node 364 is coupled to the timing circuit 352 which selectively supplies an electrical release signal from the battery 344 to the nodes. Release signals are supplied to the release nodes 364 in the order of increasing tether length so that the shortest tether is first released to allow the plunger 320 to move upwardly one increment, the next shortest tether is then released, etc. until the plunger has been forced by the spring 340 to the top of the housing 304 at the discharge end.

In the event that any tether 360 is not released, then any subsequent release node 364 activated by the timing circuit 352 will not be able to allow any further movement of the plunger 320. Nevertheless, a completion release node 366, located at the point of connection of the tethers 360 to the plunger 320, may be activated to sever or release all tethers to allow a final thrust of the plunger 320 toward the discharge end 312 of the housing. In this manner, even though one of the tethers 360 may have failed to release, activation of the release node 366 would provide for the release of all the tethers and a final movement of the plunger 320. The release node 366 may be activated after all other release nodes 365 have been activated or may remain unactivated. Whether or not release node 366 is activated is determined by the end result to be accomplished by the embodiment.

FIG. 8 shows a fragmented, side, cross-sectional view of another embodiment of a drug delivery system which also utilizes a plunger 404 slidably disposed in a housing 408. A coil spring, not shown but similar to the spring 340 of the system of FIG. 6, is also disposed in the housing 408 to bias or urge the plunger 404 upwardly toward a discharge end of the housing.

The plunger 404 is prevented from its upward movement by a single tether 412 coupled at one end to the plunger 404 and at the other end to a circuit card 416. Successive pairs of points along the length of the tether 412 are joined together by release elements 420 to thus form a series of loops 424 in the tether. The release elements join the two corresponding points of the tether 412 together until activated by release signals supplied by way of conductors 428 by a circuit pack 432. As a release element 420 is activated, for example by a pyrotechnic material represented at 421, the two adjacent points of the tether 412 joined together are released so that the effective length of the tether increases to allow an upward movement of the plunger 404. The pyrotechnic material 421 responds to electrical signals which can be generated as in the earlier described embodiments. It will be appreciated that the pyrotechnic material 421 and the release element 420 may readily be integrated into a single structure. As a next release element is activated, another loop of the tether is released so that the tether again increases its effective length to allow another upward movement of the plunger 404. In this manner, by successive application of release signals to the release elements 420, the plunger 404 is allowed successive upward movements to thereby force drug solution located above the plunger to discharge out the discharge end of the housing 408.

FIGS. 9 and 10 show a side, elevational, partially cross-sectional view and a top plan view respectively of a pyrotechnic gas generating element suitable for use in the embodiments of FIGS. 1 through 5 of the drawings. The element is disposed on a substrate or base 504 to include a pyrotechnic material 508 which ignites easily and burns in response to an electrical signal supplied over lead 512 to an igniter strip 516. Such pyrotechnic material might advantageously be composed of nitrocellulose, barium styphnate or tetrazene. The igniter strip 516 might illustratively be made of nickel chromium. Lead 512 might illustratively be copper, copper alloy or gold. The burning of the pyrotechnic material produces gas as required for forcing drug formulation from vesicles of drug delivery apparatus.

To actuate the gas generating element of FIGS. 9 and 10, an electrical signal is supplied to the conductor 512 to flow through the igniter strip 516 causing it to heat and combust the pyrotechnic material 508.

FIGS. 11 and 12 show a side, elevational view and top plan view of another pyrotechnic gas generating element which may be used in the drug delivery apparatus of FIGS. 1-5. The element is disposed on a substrate 604 which includes an electrical conductor 608 formed of aluminum. Disposed on the aluminum strip 608 is a strip of a composition 612 of palladium (about 95 percent) and ruthenium (about 5 percent) which is narrowed or pinched at 616. Disposed over and about the composition 612 is a mass of pyrotechnic material 620 as discussed earlier.

When an electrical signal is supplied to the conductor 608 and to the composition 612, the composition alloys—heats exothermally—and this reaction progresses under the pyrotechnic material to ignite it and thus produce the desired gas. The narrowed portion 616 presents greater resistance to the electrical signal to start the alloying process.

In the manner described, simple, compact drug delivery units may be provided for implantation into an animal to release successive, timed bursts of drug solution. The volume of each unit utilized for drug containment is high relative to the volumes used for containing circuitry or other elements of the units.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed:

1. An implantable drug delivery system comprising
a housing having a base end and a discharge end for holding drug solution at the discharge end,
valve means disposed at the discharge end of the housing to allow the drug solution to flow out of the valve means and out of the housing when the drug solution pressure is applied to the valve means,
piston means slidably disposed in the housing to slide between the base end and discharge end to force the drug solution toward the discharge end and out the valve means,
biasing means for urging the piston means toward the discharge end of the housing,
movement control means, connected to the piston means, for allowing successive step-wise movement of the piston means toward the discharge end of the housing in response to a plurality of release signals, and for otherwise restraining movement of the piston means, wherein said movement control means comprises
a plurality of different length tethers each having a first and second end, the different length tethers being connected at a first end to the piston means,
a plurality of release nodes located in the housing near the base end thereof, each for holding the second end of a different one of the tethers and for releasing said second end in response to a release signal, and
means for supplying release signals in a predetermined sequence to said movement control means
wherein said release signal supplying means comprises means for sequentially supplying release signals to the release nodes in the order of the shortest tether node to the longest tether node so that as a tether is released, the piston means is moved toward the discharge end of the housing to thereby discharge a bolus of drug solution from the housing, until the next shortest unreleased tether stops further movement of the piston means.

2. A system as in claim 1 wherein said release nodes are comprised of a pyrotechnic material responsive to electrical signals for combusting, and wherein said release signal supplying means generates said electrical signals.

3. A system as in claim 1 further comprising an additional release node disposed on the piston means for holding all of said first ends of the tethers and for releasing all of said first ends in response to a completion release signal, and wherein said release signal supplying means is connected to said additional release node to supply a completion release signal thereto after release signals have been supplied to the other release nodes.

4. A system as in claim 1 wherein said biasing means comprises a coil spring.

5. An implantable drug delivery system comprising
a housing having a base end and a discharge end, for holding drug solution at the discharge end,
valve means disposed at the discharge end of the housing to allow the drug solution to flow out of the valve means and out of the housing when the drug solution pressure is applied to the valve means,
piston means slidably disposed in the housing to slide between the base end and discharge end to force the drug solution toward the discharge end and out the valve means,
biasing means for urging the piston means toward the discharge end of the housing,
movement control means, connected to the piston means, for allowing successive step-wise movement of the piston means toward the discharge end of the housing in response to a plurality of release signals, and for otherwise restraining movement of the piston means, wherein said movement control means comprises a tether having first and second ends, the tether connected at the first end to the piston means and at the second end to the base end of the housing, a plurality of release elements joining together respective pairs of adjacent points along the tether to form a succession of loops in the tether which serve to shorten the effective length of the tether by increments corresponding to the loop length, said release elements being responsive to said release signals for releasing the joinder of respective pairs of points to thus allow incremental lengthening of the effective length of the tether, and means for supplying release signals in a predetermined sequence to said movement control means, wherein said release signal supplying means comprises means for sequentially supplying release signals to the release elements to allow successive effective lengthening of the tether so that the piston means is allowed to move toward the discharge end of the housing in increments to thereby successively discharge boluses of drug solution from the housing.

6. A system as in claim 5 wherein said release elements are comprised of a pyrotechnic material responsive to electrical signals for combusting, and wherein said release signal supplying means generates said electrical signals.

7. A system as in claim 5 wherein said biasing means comprises a coil spring.

* * * * *